US012152267B2

(12) United States Patent
Aymard et al.

(10) Patent No.: US 12,152,267 B2
(45) Date of Patent: Nov. 26, 2024

(54) METHOD FOR TREATING A LIGNOCELLULOSIC BIOMASS

(71) Applicants: INSTITUT NATIONAL DE RECHERCHE POUR L'AGRICULTURE L'ALIMENTATION ET L'ENVIRONNEMENT, Paris (FR); IFP Energies Nouvelles, Rueil-Malmaison (FR)

(72) Inventors: Caroline Aymard, Rueil-Malmaison (FR); Severine Louesdon-Jeunet, Rueil-Malmaison (FR); Romain Rousset, Rueil-Malmaison (FR); Damien Hudebine, Rueil-Malmaison (FR)

(73) Assignees: INSTITUT NATIONAL DE RECHERCHE POUR L'AGRICULTURE L'ALIMENTATION ET L'ENVIRONNEMENT, Paris (FR); IFP Energies Nouvelles, Rueil-Malmaison (FR)

( * ) Notice: Subject to any disclaimer, the term of this patent is extended or adjusted under 35 U.S.C. 154(b) by 73 days.

(21) Appl. No.: 17/425,418

(22) PCT Filed: Jan. 20, 2020

(86) PCT No.: PCT/EP2020/051289
§ 371 (c)(1),
(2) Date: Jul. 23, 2021

(87) PCT Pub. No.: WO2020/152105
PCT Pub. Date: Jul. 30, 2020

(65) Prior Publication Data
US 2024/0026388 A1 Jan. 25, 2024

(30) Foreign Application Priority Data
Jan. 24, 2019 (FR) ...................................... 1900597

(51) Int. Cl.
C12P 7/06 (2006.01)
C12P 7/04 (2006.01)
C12P 7/16 (2006.01)
C12P 7/28 (2006.01)

(52) U.S. Cl.
CPC ................... *C12P 7/06* (2013.01); *C12P 7/04* (2013.01); *C12P 7/16* (2013.01); *C12P 7/28* (2013.01); *C12P 2201/00* (2013.01)

(58) Field of Classification Search
CPC ...... C12P 7/06; C12P 7/04; C12P 7/16; C12P 7/28; C12P 2201/00; C12P 7/10; Y02E 50/10
See application file for complete search history.

(56) References Cited

U.S. PATENT DOCUMENTS 8,597,431 B2 * 12/2013 McDonald ............... C13K 1/02
127/1
11,299,758 B2 * 4/2022 Aymard .................. C12P 19/02
2013/0236941 A1 9/2013 Burns-Guydish et al.

FOREIGN PATENT DOCUMENTS

FR 3069248 A1 * 1/2019 ............... C08H 8/00
WO WO2018015227 A1 * 1/2018 ............... C08H 8/00

OTHER PUBLICATIONS

International Search Report dated Apr. 23, 2020 issued in corresponding PCT/EP2020/051289 application (2 pages).

* cited by examiner

Primary Examiner — Ganapathirama Raghu
(74) Attorney, Agent, or Firm — Millen, White, Zelano, & Branigan; Csaba Henter

(57) ABSTRACT

The subject of the invention is a process for treating lignocellulosic biomass comprising the following steps:
  a) conditioning the lignocellulosic biomass,
  b) washing said particles,
  c) separating the aqueous solution from the washed biomass particles,
  d) impregnating said lignocellulosic substrate with an acid liquor,
  e) carrying out a solid/liquid separation of the impregnated lignocellulosic substrate,
  f) pretreating said substrate from step e) by cooking,
  g) carrying out an enzymatic hydrolysis of the pretreated lignocellulosic substrate,
  h) carrying out a fermentation of the hydrolyzate from step g),
  and introducing the used aqueous washing solution into a step of said biomass treatment process which is after the pretreatment step f), and/or into an enzyme production step and/or into a step of producing/propagating the microorganisms necessary for steps g) or h).

20 Claims, 3 Drawing Sheets

METHOD FOR TREATING A LIGNOCELLULOSIC BIOMASS

TECHNICAL FIELD

The present invention falls within the field of processes for producing sugars from lignocellulosic biomasses. It relates more particularly to a process for treating lignocellulosic biomass for the production of alcohols or solvents useful as biofuels (for example ethanol) or for the synthesis of biobased molecules. The treatment process according to the invention may incorporate a steam explosion or acid cooking pretreatment of the lignocellulosic biomass.

PRIOR ART

Lignocellulosic biomass is composed of three main constituents: cellulose (35% to 50%), hemicellulose (23% to 32%), which is a polysaccharide essentially constituted of pentoses and hexoses, and lignin (15% to 25%), which is a macromolecule of complex structure and of high molecular weight, originating from the copolymerization of phenylpropenoic alcohols. These various molecules are responsible for the intrinsic properties of the plant wall and are organized in a complex entanglement.

Cellulose, predominant in this biomass, is thus the most abundant polymer on Earth and the one which has the greatest potential for forming materials and biofuels. However, the potential of cellulose and derivatives thereof has not been able, up to now, to be fully exploited, mainly due to the difficulty in extracting cellulose. Indeed, this step is made difficult by the very structure of the plants. The technological barriers identified to the extraction and processing of cellulose are in particular its accessibility, its crystallinity, its degree of polymerization, and the presence of hemicellulose and lignin.

The principle of the process for converting lignocellulosic biomass by biotechnological processes uses a step of enzymatic hydrolysis of the cellulose contained in plant materials in order to produce glucose.

The glucose obtained can then be fermented into various products such as alcohols (ethanol, 1,3-propanediol, 1-butanol, 1,4-butanediol, etc.) or acids (acetic acid, lactic acid, 3-hydroxypropionic acid, fumaric acid, succinic acid, etc.).

Cellulose and optionally hemicelluloses are the targets of the enzymatic hydrolysis but are not directly accessible to the enzymes. This is the reason why these substrates must undergo a pretreatment preceding the enzymatic hydrolysis step. The pretreatment aims to modify the physical and physicochemical properties of the lignocellulosic material, with a view to improving the accessibility of the cellulose trapped within the lignin and hemicellulose matrix. One of the most effective pretreatments is steam explosion which enables almost complete hydrolysis of hemicellulose and a significant improvement in the accessibility and reactivity of cellulose with respect to enzymes. This pretreatment may be preceded by other treatment(s) such as an acid impregnation. Biomass impregnated with an aqueous solution, with or without acid, is treated continuously with steam in a reactor under pressure and at temperature in order to destructure mainly the hemicellulose.

The pretreated biomass is composed of solids (mainly cellulose and lignin) and water-soluble sugars. In some process configurations, a fraction of the pretreated solid is sent to a soluble sugars extraction step in order to recover a sugary liquor. For example, the document "Lignocellulosic Biomass to Ethanol Process Design and Economics Utilizing Co-Current Dilute Acid Prehydrolysis and Enzymatic Hydrolysis for Corn Stover", Aden et al. NREL/TP-510-32438 teaches the separation of pretreated biomass into a solid fraction and a liquid fraction. This sugar-rich liquor can then be used as a source of carbon in units for enzyme production and for yeast propagation. The pretreated substrate depleted in soluble sugars can be sent to the enzymatic hydrolysis step together with the raw marc leaving the pretreatment unit.

The enzymatic hydrolysis aims to convert the pretreated substrate into monomeric sugars. The enzyme cocktail used for this step is a mixture of cellulolytic and/or hemicellulolytic enzymes capable of breaking down cellulose into a solution of sugars, containing in particular glucose. The enzymes in the enzyme cocktail contain three major types of enzymes according to their activity: endoglucanases, exoglucanases, and cellobiases. The most used microorganism for the production of the enzyme cocktail is the fungus *Trichoderma reesei*. The process for producing the enzyme cocktail begins with a propagation phase, the objective of which is to multiply the filamentous fungus *T. reesei*. Once the fungus concentration is sufficient to produce a fairly concentrated enzyme cocktail, an enzyme cocktail production phase is induced by a change of sugary substrate. At the end of this fermentation process, a must is obtained that contains a mixture of enzymes and filamentous fungus. *T. reesei*. This must can be used directly in enzymatic hydrolysis, or else the enzymes can be separated from the fungus and then optionally concentrated.

Fermentation of the sugars resulting from the enzymatic hydrolysis into various products such as alcohols, solvents or acids requires the use of biocatalysts (bacteria or yeasts). Although the main target of the fermentation step is the conversion of sugars into bioproducts, and the conditions of the fermentation step are chosen to promote this metabolic pathway, carrying out a fermentation step necessarily involves parallel reactions that target the growth and maintenance of the fermentation microorganisms. For example, Pasteur showed in the 19th century that about 5% of the sugars are converted into coproducts, or used for cell maintenance and growth, in the case of the fermentation of glucose into ethanol by the yeast *Saccharomyces cerevisiae*.

The sugary liquor resulting from the step of extracting the pretreated marc can be used partially or completely for the production of the biocatalysts. This sugar-rich substrate is brought into contact with an inoculum of yeasts or bacteria under conditions favorable to their multiplication. Biocatalyst production requires the introduction of carbon-containing and nitrogen-containing compounds, but also of mineral elements and vitamins. The requirements vary depending on the type of biocatalyst considered. At the end of growth, the must obtained containing the yeasts or bacteria is used directly without separation in the fermentation step, or alternatively this must can be concentrated, for example by centrifugation.

These alcohol production processes to produce in particular biofuel (ethanol) by fermentation therefore comprise, in a known manner, the following sequence of steps: grinding the biomass, optionally impregnating the biomass, then pretreating by steam explosion or cooking under acidic conditions, enzymatic hydrolysis to produce sugars or biobased molecules and alcoholic fermentation to produce biofuel alcohols such as ethanol or another type of fermentation to produce biobased molecules, the ethanol (or the biofuels or biobased molecules) then being separated for example by distillation.

U.S. Pat. No. 8,545,633 describes such a process for producing ethanol with conventional operating conditions for these steps, which conditions are known to those skilled in the art. This patent more particularly teaches methods of treating the ground biomass before impregnation.

A first treatment method is an injection of steam (referred to as "pre-steaming") into the particles of ground biomass in order to homogenize the biomass and prevent the formation of pockets which are poorly impregnated. This treatment is carried out with steam at 110° C. or more and at at least 1.3 bar absolute (5 psig) at a rate of 10 to 20 kg/h for 5 to 30 minutes. A small amount of dilute acid can be introduced, for example 0.5 to 15 g acid/kg of biomass. Another method consists in removing the fraction of fine particles rich in ash from the biomass. The fines are separated by a physical separation based on particle size, and these fines are richer in "ash" than the initial biomass. This "ash" is composed of minerals: silica, compounds containing calcium, magnesium, sodium, potassium, phosphorus and/or aluminum. During acid impregnation, the ash can consume the acid to form salts, which makes it necessary to increase the amount of acid during impregnation. It represents 1% to 10% by weight of the biomass, a portion of it is insoluble in the acid (silica is the major portion of the insolubles).

One method for measuring the ash of lignocellulosic products is described, for example, in the standard ASTM E1755 "Standard Test Method for Ash in Biomass". This same document describes two processes for removing this ash, namely washing with water, which is not recommended, and a dry treatment, which is recommended.

The dry process uses the techniques of separation by air jet or cyclone, by dry screening, dry filtration, sedimentation in several steps, each separating increasingly fine particles, the ash being found in the smallest particles. Thus, 95% of the biomass particles sent for impregnation have a size greater than 250 μm and at least 60% of them have a size less than 4 mm. The aim of this type of separation is to obtain, with a view to impregnation, a biomass having an ash content of less than 10% by weight, which corresponds to a reduction of at most 75% of the initial ash content, and of this ash, at least 40% is ash that is soluble in the acid (used for the impregnation). The water content of the biomass is at most 20% by weight, which corresponds to a dry matter content of at least 80% by weight.

The water washing process, and even the use of water in the dry process, is strongly discouraged in U.S. Pat. No. 8,545,633 for several reasons. This is because water can dissolve the soluble compounds of the biomass, such as cellulose, hemicellulose and starch, which reduces the sugar and ethanol yields. Furthermore, since the amount of water absorbed by the biomass is large, this would result, on the one hand, in a reduced dispersion of the acid in the biomass during impregnation and, on the other hand, the need to use much higher concentrations of acid, resulting in greater corrosion risks. In addition, the resulting amounts of water and acid to be reprocessed are substantial and lead to significant additional costs.

SUMMARY OF THE INVENTION

Completely contrary to the teaching of U.S. Pat. No. 8,545,633, the process for treating lignocellulosic biomass according to the invention uses washing with water before the impregnation step, with a washing which is carried out under given conditions, making it possible to avoid the drawbacks presented above while reducing the consumption of acid used for the impregnation step, in which the waste water resulting from the washing is also advantageously made use of.

The subject of the invention is a process for treating lignocellulosic biomass comprising the following successive steps:

a) conditioning the lignocellulosic biomass by at least one grinding step, in particular so as to obtain particles of ground biomass having a size of at most 300 mm;

b) washing said particles with an aqueous solution having a pH of between 4 and 8.5, at a temperature of between 10° C. and 95° C., at atmospheric pressure, and for a period of between 1 and 300 minutes;

c) separating the aqueous solution from the washed biomass particles in order to obtain, on the one hand, a lignocellulosic substrate having a dry matter content of between 15% and 70% by weight, and, on the other hand, a used aqueous washing solution;

d) impregnating said lignocellulosic substrate with an acid liquor, so as to obtain an impregnated lignocellulosic substrate having a pH of between 0.1 and 3;

e) carrying out a solid/liquid separation of the impregnated lignocellulosic substrate, in order to obtain, on the one hand, a lignocellulosic substrate having a dry matter content of between 15% by weight and 70% by weight, and, on the other hand, a liquid effluent;

f) pretreating said impregnated lignocellulosic substrate resulting from step e) by cooking, in particular for a period of between 1 and 120 minutes, so as to obtain a pretreated lignocellulosic substrate;

g) carrying out an enzymatic hydrolysis of the pretreated lignocellulosic substrate with enzymes produced from fungus-type microorganisms, so as to obtain a hydrolyzate containing sugars;

h) carrying out a fermentation, by bacteria- or yeast-type microorganisms, of the hydrolyzate resulting from step g) in order to obtain a fermentation must containing at least one biobased molecule such as a solvent and/or an alcohol;

optionally integrating into said process a step of producing enzymes and/or a step of producing/propagating the microorganisms necessary for steps g) or h), and introducing at least one portion of the used aqueous washing solution separated in step c) into a step of said biomass treatment process which is after the pretreatment step f), and/or into an enzyme production step and/or into a step of producing/propagating the microorganisms necessary for steps g) or h) when at least one of these enzyme production and/or microorganism production/propagation steps is integrated into said biomass treatment process.

Within the context of the invention, the content of dry matter (DM) is measured according to the standard ASTM E1756-08(2015) "Standard Test Method for Determination of Total Solids in Biomass".

The expression "at least one portion of the used washing solution" is understood to mean either the whole of said solution, thus 100% of this solution is recycled in the process to the steps mentioned above, or only one portion, the remainder being simply purged or recycled to a step of the process different from those mentioned above.

It is also in accordance with the invention to recycle the whole of this solution to at least two chosen steps according to the invention (after the pretreatment, and/or enzyme production, and/or microorganism production).

The invention therefore proposes to add a washing of the biomass with an aqueous solution, then a solid/liquid separation, before carrying out the pretreatment, and, in addition, making use of the washing water which results therefrom, with a twofold advantage. The biomass thus washed and then separated is depleted in ash, which will make it possible to significantly reduce the acid consumption of the process during the impregnation step. Conversely, the used washing water will itself become enriched in ash, and this characteristic makes it possible to use it in steps of the process where the presence of minerals in the liquid phase is an advantage, as described in detail below.

And, surprisingly and contrary to the teaching of the prior art, this washing, carried out under the specific conditions recommended in the invention, did not lead to excessive overconsumption of water or other processing problems. It should be noted, in particular, that the pH of the washing solution should be adjusted to at least 4 (therefore to a minimum pH that is very different and much higher than the acid impregnation pH), and which can be moderately acidic, moderately basic or neutral. Such a moderate pH of the washing solution has proved to be particularly suitable, and has justified in particular the choice made in the invention to reuse the used washing solution after the pretreatment step, in steps where the pH is not very acidic.

The fact that the washing is carried out at atmospheric pressure ensures that it is indeed an aqueous solution in the liquid phase that is present, and not a vapor. The washing time, of at most 300 minutes, makes it possible to obtain the desired ash depletion of the biomass, without excessively affecting the overall production time. The washing temperature is within a range that makes it possible either to use tools and an aqueous solution at ambient temperature, or to moderately heat for example only the aqueous solution, depending in particular on the type of biomass.

Preferably, according to a first embodiment, at least one portion, or all, of the used aqueous washing solution separated in step c) is introduced into the enzymatic hydrolysis step g) or into the fermentation step h).

It has turned out that it is in the fermentation step that the introduction of the used washing water is the most beneficial: this introduction can be carried out directly in the fermentation step h), or can be carried out upstream of the fermentation step, in the neutralization step (if this is provided) or enzymatic hydrolysis step: the remaining mineral salts are thus transferred to the fermentation step where they can play their role. The salts may however be at least partly modified when they are introduced from the enzymatic hydrolysis or from the neutralization, due to the change in the pH of the reaction medium. The minerals are in particular advantageous for the parallel reactions that target the maintenance and/or the growth of the microorganism used in the fermentation step.

According to one embodiment, the method according to the invention also comprises a step of neutralizing the lignocellulosic substrate pretreated in step f), before or during the enzymatic hydrolysis step g), and at least one portion, or all, of the used aqueous washing solution separated in step c) is introduced into said neutralization step.

Preferably, the neutralization step is carried out so that the pH of the enzymatic hydrolysis reaction mixture is preferably between 4 and 6. It is thus seen that the used aqueous solution has a pH that is compatible with that targeted in this neutralization step.

According to one embodiment of the invention, the process also comprises an integrated step of producing, by fungus-type microorganisms, the enzymes necessary for the enzymatic hydrolysis of step g), and at least one portion, or all, of the used aqueous washing solution separated in step c) is introduced into said enzyme production step.

Throughout the present text, a step that is "integrated" into the process of the invention is understood to mean a step for producing a compound intended to treat the biomass, such as an enzyme or a yeast, before it is brought into contact with said biomass, in the same plant or in the vicinity of the plant carrying out the treatment of the biomass: it is thus an "in situ" production of compounds of biological origin which will be used in the treatment of the biomass (alternatively, these compounds of biological origin can be produced off-site, and brought to the biomass treatment plant).

According to one embodiment, the process according to the invention also comprises an integrated step of propagating bacteria- or yeast-type microorganisms necessary for the fermentation of step h), and at least one portion of the used aqueous washing solution separated in step c) is introduced into said propagation step.

In the case of the production of enzymes, as in the case of the production of bacteria or yeasts mentioned above, the use of the used aqueous washing solution is very advantageous, because its moderate pH is compatible with that targeted in the reaction media involved (in particular a moderately acidic pH). And in addition, it turns out that this mineral-enriched solution is favorable to the production of the targeted enzymes or microorganisms, these minerals constituting nutrients for the microorganisms concerned.

Preferably, the duration of washing step b) is between 1 and 60 minutes, and preferably between 1 and 15 minutes. This washing has proven to be effective even with a short duration, which is an advantage industrially.

Preferably, the aqueous solution of step b) for washing the particles has a pH of between 5.5 and 7.5, in particular between 6 and 7.5 or between 6.5 and 7.5. In a preferred embodiment, the aqueous washing solution is therefore close to a neutral pH, which makes it possible to simply use water without addition of acid or base, without reducing the performance of the washing.

Preferably, the aqueous solution of step b) for washing the particles is at a temperature of between 25° C. and 95° C., in particular between 30° C. and 60° C. Depending on the thermal conditions in the plant, this washing can therefore be carried out at ambient temperature or with moderate heating, in particular provided by heating the solution before bringing it into contact with the biomass (or by recycling water from another step of the process, water that is in fact in this temperature range without additional heat input).

Advantageously, the amount of aqueous solution supplied to the washing step b) is between 0.5 and 60 g/g biomass. It is preferably between 1 and 30 g/g biomass, and in particular between 1.5 and 20 g/g biomass.

According to the invention, it is also possible to reintroduce a portion of the used aqueous washing solution separated in step c) into the washing step b).

According to a preferred variant of the invention, the steps g) of enzymatic hydrolysis and h) of fermentation are concomitant, they are then referred to as SSCF for the acronym of "Simultaneous saccharification and co-fermentation".

Optionally, a portion of the liquid effluent resulting from step e) can be introduced into the washing step b). Since this effluent is acidic, its contribution should be moderate in order to remain within a pH range appropriate for the washing solution.

According to one embodiment of the invention, in step f), a steam explosion pretreatment is carried out in order to obtain a vapor and the pretreated lignocellulosic substrate, the vapor resulting from step f) is condensed so as to produce an acid condensate. The steam explosion pretreatment preferably lasts at most 30 minutes, in particular at most 15 minutes.

At least one portion of the acid condensate, alone or as a mixture with water, can be introduced into the washing step b). The supply of condensate should be adjusted so that the washing solution remains within the recommended pH range.

Preferably, said biomass particles, once ground in step a) have a size of at least 1 mm.

Preferably, the lignocellulosic substrate resulting from step c) is sent directly to the impregnation step d).

The lignocellulosic substrate resulting from step c) preferably has a dry matter content of between from 25% to 70% by weight, more preferably of between 40% and 65% by weight.

Preferably, the impregnation step d) is carried out in a single step with a residence time of from 10 seconds to 180 minutes.

Preferably, the lignocellulosic substrate resulting from step e) has a dry matter content of between 40% and 65% by weight.

In an alternative embodiment already mentioned above, the process also comprises integrated steps for the production of biocatalysts: fungus, enzymes, bacteria or yeasts. These production steps may preferably be carried out with a growth of the microorganism(s) from a sugary liquor resulting from the biomass treatment process. This sugary liquor can be extracted after the pretreatment step f), it then contains monomeric sugars resulting from the solubilization of the hemicelluloses which takes place during the pretreatment f). This sugary liquor can be extracted after the enzymatic hydrolysis step g), it then also contains the monomeric glucose which is the product of the enzymatic hydrolysis of the cellulose. Preferably, the extraction of the sugary liquor takes place between the pretreatment step f) and the enzymatic hydrolysis step g). The sugary liquor can be extracted by a washing of the pretreated substrate. Advantageously, at least one portion of the stream used for the washing can be the used washing water resulting from step c).

The invention therefore optionally makes provision for integrating into said process a step of producing enzymes and/or a step of producing/propagating the microorganisms necessary for steps g) or h), and for providing a step of extracting at least one portion of the sugary liquors obtained after the pretreatment step f) or after the enzymatic hydrolysis step g), in particular by washing the substrate with an aqueous solution. Preferably, in this scenario, it is possible to introduce at least one portion of the used aqueous washing solution resulting from step c) for the extraction, by washing, of the sugary liquors.

The process according to the invention can be carried out for the production of ethanol or an acetone-butanol-ethanol (ABE) mixture or an isopropanol-butanol-ethanol (IBE) mixture or any other biobased molecule or solvent, such as acetone.

LIST OF FIGURES

Figure 4:
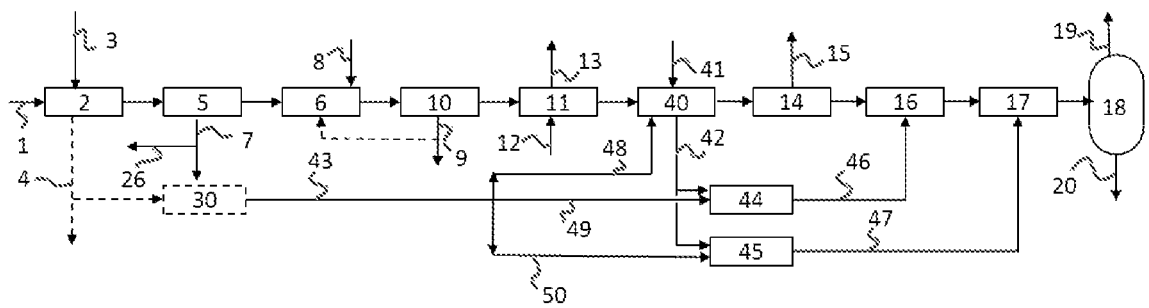

FIG. 4 is a block diagram representing yet another embodiment of the process for producing solvents and/or alcohols according to the invention which comprises units for the in situ production of enzymes and yeasts; incorporating a recycling of the water used for the washing of the ground biomass to the production of biocatalysts and/or for the extraction of a sugary liquor at least partly used for the production of biocatalysts.

Figure 5:
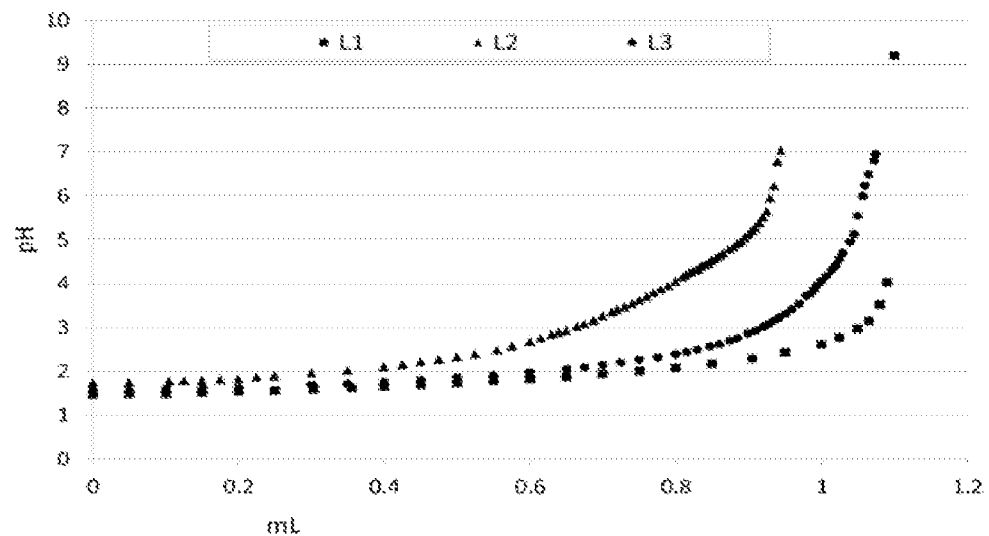

FIG. 5 shows the acid-base titration curves of the liquors of example 1.

Figure 6:
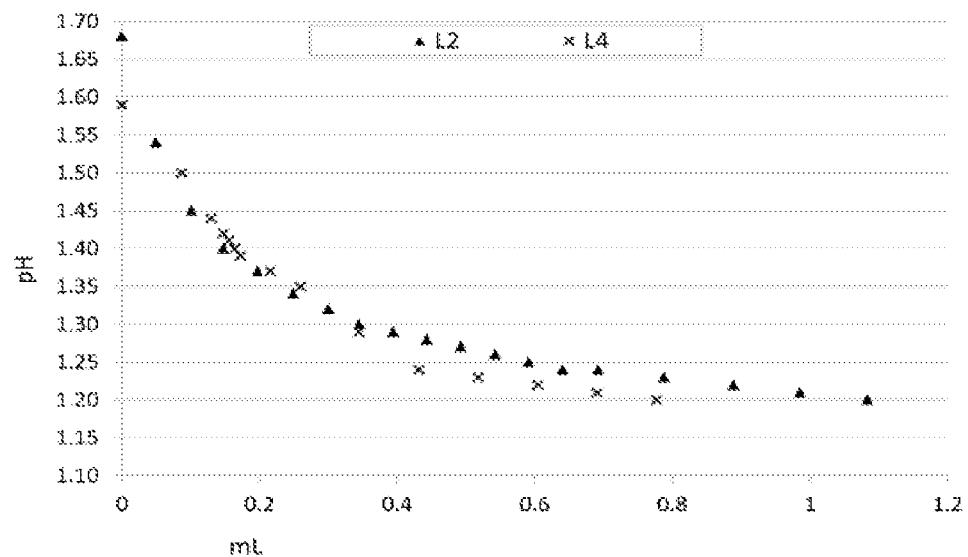

FIG. 6 shows the change in the pH as a function of the specific volume of sulfuric acid $H_2SO_4$ solution added to the used impregnation liquors of example 2.

Figure 7:
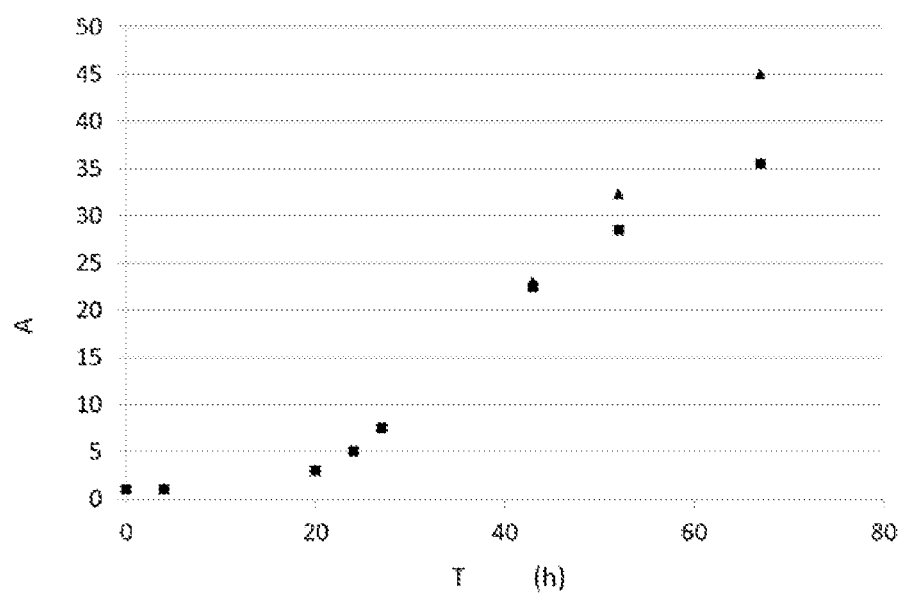

FIG. 7 shows the change in the absorbance during the growth of yeasts in the culture media with or without minerals of example 5.

DESCRIPTION OF THE EMBODIMENTS

Described in detail below are the various steps of biomass treatment in accordance with one embodiment of the invention described above:

Step a) of Conditioning the Lignocellulosic Biomass

The treatment process comprises, in its first step, a step of conditioning the lignocellulosic biomass with at least one grinding so as to obtain biomass particles having a size of at most 300 mm. It is of course possible to carry out several successive grinding steps in order to reach the targeted particle size. In general, the ground biomass has a particle size (the largest size) of at most 300 mm, usually at least 1 mm, and often between 2 and 200 mm. Any method known to those skilled in the art can be used to carry out this step. Usually, straw is ground with screens of from 5 to 100 mm. With regard to wood, it is generally chipped into parallelepipedal chips with a length of between 20 and 160 mm, a width of between 10 and 100 mm and a thickness of between 2 and 20 mm.

The ground lignocellulosic biomass is conveyed to the washing step (zone) by any means known to those skilled in the art, in particular a screw conveyor.

Step b) of Washing the Ground Lignocellulosic Biomass

It is necessary to carry out a step of acid impregnation of the biomass in order to increase its reactivity in the pretreatment step. However, in the case of certain lignocellulosic biomasses such as straw and *miscanthus*, an overconsumption of acid was observed during this impregnation step. According to the prior art, this would be associated with the basic nature of these biomasses which require excess acid to neutralize the basic elements constituting the biomass.

The applicant has now found that the determining effect on the consumption of acid would not be a basicity effect but rather a buffer effect due to the presence of acetic acid or its salts which are generated by the solubilization of the ash contained in the ground lignocellulosic biomass when it is brought into contact with the acidic aqueous solution used for the impregnation step. Due to the high pKa (4.76 at 25° C.) of acetic acid compared to the pH of the acidic impregnation solution (pH<3 and usually less than 2), acetic acid has a buffer effect on the pH, requiring the supply of large amounts of acid to bring the pH to a value compatible with the acid pretreatment step, which is generally between 0.1 and 3.

According to the invention, a step (step b) of washing the ground biomass particles is carried out with an aqueous washing solution, at a temperature between 10° C. and 90° C., preferably at atmospheric pressure.

The pH of the aqueous washing solution is between 4 and 8.5, and more preferentially between 6 and 7.5. The aqueous washing solution can be acidified, advantageously by the impregnation acid which is used in the impregnation step d) described in detail below. Alternatively and preferably, the optional acid is not added to the washing water by an external input, but comes from a process stream containing said acid. In the context of the invention, it is not necessary to add other compounds (basic compounds, complexing compounds, etc.) to the aqueous washing solution used in step b). The aqueous washing solution can also be simply water (neutral pH). The aqueous solution can be an aqueous stream recycled from the process. It is also noted that, according to the invention, the washing step b) is carried out in the absence of water in the vapor state.

All methods of washing in a single step or in several steps in a co-current, counter-current or cross-current mode are possible. By way of illustration, the washing can be carried out by soaking, for example by transfer of the biomass through a water bath, or else under a flow of water, for example by a distribution of water running over the biomass which is optionally set in motion.

The amount of water used for this step is preferably as low as possible in order to obtain the desired effect. The washing is carried out using between 0.5 and 60 g of water/g of lignocellulosic biomass, preferably between 1 and 30 g of water/g of biomass and more preferentially between 1.5 and 20 g of water/g of biomass. For example, the quantity of washing water to be used can be determined by means of a laboratory test preceding the biomass treatment run and consisting in measuring the pH of the used washing water (or filtrate) recovered after the washing step.

Preferably, the tool(s) carrying out the washing do not have heating equipment, and the washing temperature is regulated by the temperature of the aqueous washing solution. The temperature of the aqueous washing solution is between 25° C. and 95° C. and preferentially between 30° C. and 60° C., it may therefore be just at ambient temperature, or have been heated, for this specific washing step or because it comes, at least in part, from the recycling of liquid effluents produced in the process and that are already in this temperature range.

The washing time is between 1 minute and 300 minutes, and preferentially between 1 minute and 60 minutes, and more preferentially still between 1 minute and 15 minutes.

Step c) of Separating the Used Washing Water

The process comprises a step of separating the liquid from the particles of washed lignocellulosic biomass in order to obtain a lignocellulosic substrate, the dry matter content of which is between 15% and 70% by weight (measured according to the standard ASTM E1756), preferably between 25% and 70% and more preferably between 40% and 65% by weight. Any liquid/solid separation method can be used, provided that the dry matter content at the end of this step is respected. For example, the solid/liquid separation is carried out by a filter press type tool or performed by draining, for example by gravity.

Preferably, the step of separating the used washing water is carried out concomitantly with the transfer of the washed lignocellulosic biomass to the impregnation step, by means of a screw conveyor comprising a zone of solid/liquid separation by pressing of the solid material. This type of screw conveyor, referred to as a "sealing screw feeder" or "plug screw feeder", comprises a conical compression zone allowing the formation of a hermetic plug of washed biomass and a perforated zone allowing the discharge of the used washing water.

When, in normal operation, the tool chosen to carry out this separation does not make it possible to directly extract a sample of the biomass, the dry matter (DM) content can be determined by calculation: it is then considered that the DM contained in the pressed sample is the difference between the DM of the washed biomass at the inlet and the DM present in the liquor extracted during pressing, the calculation therefore requires a measurement of the mass flow rates of the washed biomass at the inlet and of the liquor extracted, and DM measurements of samples of washed biomass at the inlet and of liquor extracted at the outlet (for example according to the same standard ASTM E1756). The calculation is made as follows: let ABI be the amount by weight of biomass at the inlet, % DMBI the dry matter content expressed in % of the washed biomass at the inlet, let ALQ be the amount by weight of liquor extracted and % DMLQ the dry matter content expressed in % of the liquor extracted, the DM content of the pressed substrate is obtained from the difference by applying the formula: DM pressed substrate= (ABI*% DMBI−ALQ*% DMLQ)/(ABI−ALQ)

The separation step c) thus makes it possible to provide a used washing water, at least one portion of which can advantageously be used in a downstream step, in particular the downstream fermentation step, according to the process for treating lignocellulosic biomass according to the invention as described below with reference to FIGS. 1 to 4 described in detail below. One portion of the used washing water may be recycled to the washing step b) of the process and the other portion used in a downstream step. The used washing water can optionally be mixed with another filtrate resulting from another step of the process, before being recycled for example to the washing step b).

The separation step c) can be carried out in one or more steps. The separation step c) can also be carried out concomitantly with the washing step b), in a tool making it possible to carry out the washing and the solid/liquid separation in a single step. This tool can be for example a rotary drum or a belt filter.

The lignocellulosic substrate resulting from the step of separating the washed biomass is sent to step d) of impregnation with an acid liquor. Preferably, the lignocellulosic substrate is sent directly to the impregnation step, that is to say that it does not undergo any other treatment before the impregnation step.

Step d) of Impregnation with an Acid Liquor

The treatment process according to the invention comprises a step d) of impregnating the lignocellulosic substrate with an acid liquor, so as to obtain a washed and impregnated lignocellulosic substrate, the pH of which is between from 0.1 to 3. This step aims to prepare the lignocellulosic substrate for the pretreatment step.

The impregnation is carried out in an impregnation reactor at a temperature between 10° C. and 90° C., and preferably at atmospheric pressure. Preferably, the impregnation is carried out at a temperature between 50° C. and 85°

C. The residence time of the lignocellulosic substrate in the impregnation reactor is usually from 10 seconds to 180 minutes, preferably between 30 seconds and 60 minutes, and more preferentially still between 30 seconds and 15 minutes. Preferably, the impregnation step is performed in a single step. Preferably, the washed and impregnated lignocellulosic substrate has a pH of between from 0.9 to 2.5.

The impregnation reactor or impregnator is generally equipped with one or more screws which transfer the lignocellulosic substrate from its inlet to the outlet opening. The impregnator is moreover equipped with one or more lines for conveying the acid liquor and also, if need be, one or more lines for withdrawing acid liquor. Said acid liquor inlet and outlet lines are generally installed so as to function by cocurrent or counter-current recycling.

The acid liquor is an aqueous solution of a strong acid, which is for example chosen from sulfuric acid, hydrochloric acid and nitric acid, for example at an acid content of between 0.5% and 4% by weight. Preferably, the acid used is sulfuric acid.

Step e) of Solid/Liquid Separation on the Lignocellulosic Substrate Impregnated with Acid Liquor In accordance with step e) of the treatment process according to the invention, the lignocellulosic substrate impregnated with acid liquor is subjected to a solid/liquid separation step in order to obtain a lignocellulosic substrate having a dry matter content of between 15% and 70% by weight and a used acid liquor. Preferably, the lignocellulosic substrate impregnated with acid liquor is first drained, in order to extract at least a portion of the free acid liquor, before being treated by solid/liquid separation.

The solid/liquid separation step may implement any technique known to those skilled in the art, for example decantation, centrifugation or pressing.

Preferably, pressing of the lignocellulosic substrate is carried out concomitantly with its transfer to pretreatment step f), when the latter carries out the steam explosion process which is described below. This method of carrying out step e) is for example performed by a screw referred to as a "plug screw feeder", the operation of which has already been described above. The formation of a plug of pressed lignocellulosic substrate ensures the pressure-tightness of the steam explosion reactor, thus preventing steam leakage. The screw conveyor is also provided with one or more lines for withdrawing the used liquor (referred to as pressate) separated during the pressing. The pressate can be recycled to the impregnation step d) and/or to the washing step b).

The wet biomass obtained at the end of the solid/liquid separation step e), which can be denoted by the term "washed and acidified lignocellulosic substrate" has a dry matter content preferably between 25% and 70% by weight, and more preferentially between 40% and 65% by weight.

Step f) of Pretreating the Washed and Acidified Lignocellulosic Substrate

The washed and acidified lignocellulosic substrate undergoes a pretreatment step f).

Cellulose (and optionally hemicelluloses) which are the targets of the enzymatic hydrolysis are not directly accessible to the enzymes. This is the reason why a pretreatment of the biomass is carried out before the enzymatic hydrolysis step. The pretreatment is notably directed toward modifying the physical and physicochemical properties of the cellulosic fraction, such as its degree of polymerization and its state of crystallinity.

Various types of pretreatment are known to those skilled in the art, they combine a chemical treatment and a heat treatment. Mention may in particular be made of acidic or basic cooking, the "Organosolv" process, treatments with ionic liquids and the steam explosion process.

The preferred pretreatment process is steam explosion (or "SteamEx") carried out in an acidic medium. This is a process in which the lignocellulosic substrate is rapidly brought to a high temperature by injecting pressurized steam. Stoppage of the treatment takes place by abrupt decompression.

The operating conditions of the steam explosion process are as follows:
steam is injected directly into the reactor;
the temperature of the reactor is generally between 150° C. and 220° C., preferably between 170° C. and 210° C.,
the pressure is between 5 and 25 bar absolute, more preferentially between 8 and 19 bar absolute,
the residence time before the expansion phase ranges from 10 seconds to 15 minutes and preferably between 3 minutes and 12 minutes.

The steam explosion may be performed in batch or continuous mode and the depressurization step which permits destructuring of the biomass may proceed in one or more steps. Preferably, the steam explosion is carried out continuously.

At the end of the steam explosion pretreatment step, a pretreated lignocellulosic substrate with a high dry matter content, generally between 20% and 70% by weight, and usually between 35% and 65%, and a vapor phase which is then condensed, are obtained.

The implementation of steps a) to f) according to the present invention therefore makes it possible to produce a reactive pretreated substrate and a used biomass washing water. It has also been demonstrated that the process according to the present invention produces a pretreated substrate depleted in minerals compared to the processes of the prior art, in particular the processes that use a recycling of the impregnation liquor extracted in step e) to the impregnation step d). These minerals are extracted in the used washing water resulting from step c) of the process according to the present invention.

In the context of the invention, the pretreated lignocellulosic substrate obtained at the end of step f) of the treatment process according to the invention is advantageously used as feedstock in a "second-generation" process for producing solvents and/or alcohols from lignocellulosic biomass which continues the treatment of the biomass according to the successive steps described above.

Following the steam explosion under acidic conditions, the pretreated lignocellulosic substrate generally has a pH lower than that which is compatible with the medium for enzymatic hydrolysis. Thus, the lignocellulosic substrate treated according to pretreatment step f) is subjected to a neutralization step to bring its pH to a value between 4 and 6.

For the neutralization step, an aqueous solution is used that contains a neutralizing agent which can be chosen from all weak or strong bases known to those skilled in the art. The term base denotes any chemical species which, when it is added to water, gives an aqueous solution with a pH of greater than 7. Preferably, the neutralizing agent is chosen from potassium hydroxide, sodium hydroxide, aqueous ammonia and lime. More preferably still, the neutralizing agent is chosen from potassium hydroxide and aqueous ammonia, alone or in combination with one another. Preferably, the neutralizing agent is used in aqueous solution, with a weight concentration of between 2% and 75%, and more preferably still between 15% and 50%.

Neutralization is carried out at a temperature between 15° C. and 95° C., and preferably between and 70° C. In general, the temperature of the neutralization step is not precisely controlled and is simply governed by the heat given off by the acid-base neutralization reaction.

The neutralization step can be carried out continuously, in batch mode or in fed-batch mode.

It should be noted that a washing step can advantageously be carried out before or after the neutralization step, on all or part of the pretreated lignocellulosic substrate.

If a washing is applied, a liquid stream is brought into contact with the pretreated lignocellulosic substrate, then the liquid is separated from the solid. The washing step can be carried out by percolation, by successive mixing and liquid/solid separation operations, by washing on a belt filter or by any other technique known to those skilled in the art. The washing liquid used can be water or a process stream. The weight ratio between the washing liquid added and the liquid contained in the substrate to be washed is generally between 0.5 and 4. The washing step generates a sugary washing liquor containing a portion of the hemicelluloses solubilized during the pretreatment. This washing liquor can for example be used as a source of carbon for the production of biocatalysts (enzymes and/or microorganisms). The washing step is generally carried out at a temperature between 10° C. and 95° C., and preferentially between and 70° C. In a preferred embodiment, the washing stream is at least partly composed of the used washing water resulting from step c) of solid/liquid separation on the washed biomass.

Step g) of Enzymatic Hydrolysis

The pretreated lignocellulosic substrate, optionally neutralized and washed, is sent to the enzymatic hydrolysis step g) of the process.

The pretreated lignocellulosic substrate which is sent to the enzymatic hydrolysis step has a dry matter content generally of between 15% and 70% by weight.

The objective of the enzymatic hydrolysis is to hydrolyze (depolymerize), by means of biocatalysts, the hemicelluloses and cellulose into fermentable sugars, preferably glucose.

The enzymatic hydrolysis step is carried out under mild conditions, at a temperature of the order of 40° C. and 55° C., preferably between 45° C. and 50° C. and at a pH of from 4.0 to 5.5, and more preferentially still between 4.8 and 5.2. The dry matter content of the enzymatic hydrolysis medium is between 5% and 45% by weight, preferably between 10% and 30% by weight. The enzymatic hydrolysis is carried out by means of enzymes produced by a microorganism.

Use may be made of natural or genetically modified microorganisms, such as the fungi of the genera *Trichoderma, Aspergillus, Penicillium* or *Schizophyllum*, or anaerobic bacteria of, for example, the genus *Clostridium*, producing a cocktail of enzymes containing in particular cellulases and hemicellulases, suitable for extensive hydrolysis of cellulose and hemicelluloses.

The enzymatic hydrolysis can be carried out continuously or in batch mode or in fed continuous (fed batch) mode, in one or more reactors. The residence time is between 12 hours and 200 hours and preferably between 24 hours and 160 hours and more preferentially still between 48 hours and 120 hours.

At the end of step g), a hydrolyzate containing fermentable sugars is recovered from the bioreactor, which hydrolyzate is then treated in the fermentation step h).

It should be noted that the hydrolyzate obtained can optionally undergo one or more treatment steps before the fermentation step. For example, these may be a return to the pH, a partial purification with a view to limiting the content of inhibitor compound for the fermentation microorganism, or an at least partial separation of the solid residues contained in the hydrolyzate.

Step h) of Fermentation of the Hydrolyzate

According to step h) of the process for producing solvents and/or alcohols, the hydrolyzate optionally treated is sent to the fermentation step h) enabling the conversion, by means of one or more microorganisms of different genera, of the fermentable sugars into solvent and/or alcohols of interest. The fermentation methods are known to those skilled in the art and are described in particular in document U.S. Pat. No. 8,456,633.

The term "solvent" is intended to denote organic compounds other than alcohols, for example organic compounds having a ketone function such as acetone.

The term "alcohol" denotes in particular ethanol, propanol, isopropanol and butanol.

The natural or genetically modified microorganisms can be chosen, for example, from *Saccharomyces cerevisiae, Schizosaccharomyces pombe, Saccharomyces uvarum, Saccharomyces diastaticus, Kluyveromyces fragilis, Candida shehatae, Pichia stipitis, Pachysolen tannophilus* or the bacteria *Zymomonas mobilis, Clostridium acetobutylicum, Escherichia coli*.

In the context of the invention, the fermentation step makes it possible, for example, to produce ethanol alone or as a mixture with butanol, propanol, isopropanol and/or acetone. For example, the fermentation microorganism may be capable of producing an "ABE (acetone-butanol-ethanol)" mixture or else an "IBE (isopropanol-butanol-ethanol)" mixture.

Preferably, the microorganism chosen is a natural or genetically modified yeast of the genus *Saccharomyces* capable of producing ethanol.

At the end of step h), a fermentation must, diluted in products of interest, is recovered.

According to one embodiment of the process, steps g) and h) are carried out at the same time, in at least one and the same bioreactor, so that the enzymatic hydrolysis and the fermentation are carried out simultaneously according to a process denoted by the term "Simultaneous Saccharification and Fermentation (SSF)" or else "Simultaneous Saccharification and Co-Fermentation" (SSCF) when the microorganism used is capable of jointly assimilating C5 sugars and C6 sugars (for example glucose and xylose). When the hydrolysis step is merged with the fermentation step, the operating conditions, in particular temperature conditions, can be adapted to be compatible with the tolerances of the fermentation microorganism. For example, the temperature can be lowered between 28° C. and 45° C., and preferably between 30° C. and 35° C., when the fermentation is carried out with a yeast of the genus *Saccharomyces*. The pH is preferably adjusted between 5 and 5.5 in order to promote the performance of the yeasts.

In the context of the invention, the used washing water recovered in the washing step b) after separation of the biomass is advantageously used at least in part in the fermentation step h).

For this, the used washing water resulting from step c) can be introduced directly into the fermentation step h), or be introduced into the enzymatic hydrolysis step g) or even into the neutralization step prior to the enzymatic hydrolysis when it is provided. Thus, the used washing water is then transferred in part with the stream resulting from the hydrolysis which is sent to fermentation.

The use of a portion of the used washing water in fermentation makes it possible to restore to this step a portion of the minerals present in the native biomass which were removed during the washing of step b). These minerals have a beneficial impact on the growth of the microorganism used in the fermentation step. In particular, these minerals have a beneficial impact on the growth of yeast *Saccharomyces*.

The production unit carrying out the process according to the invention may comprise, in addition to the plants already described, units for the in situ production of enzymes and/or yeasts. For this type of unit, it is possible to send at least one portion of the used washing water to these enzyme and/or yeast production units in order to reuse the minerals contained therein. Before such recycling, the used washing water can be detoxified, in order to eliminate therefrom the compounds which inhibit the microorganisms, and/or readjusted in terms of pH.

The steps for producing biocatalysts require the provision of substrates making it possible to supply the elements constituting the microorganisms. These elements are mainly carbon, oxygen, hydrogen, then, secondly, nitrogen, phosphorus and sulfur. Finally, the minerals are also present in small amounts in the microorganisms. Thus, when the cells of the microorganisms multiply, they draw all the elements incorporated in their composition from their medium. The steps for producing biocatalysts are generally carried out on substrates containing assimilable carbon molecules, such as sugars, and in stirred and aerated reactors, the air making it possible to supply oxygen. In addition, supplements must be put in place to ensure the provision of the other elements such as nitrogen, phosphorus, sulfur and the minerals. In particular, the minerals may be elements that are expensive to introduce, even if the amounts involved are small. In a configuration known to those skilled in the art, the microorganisms necessary for the bioconversion process are produced in situ from sugary liquor resulting from the process. These sugary liquors are extracted either by washing the pretreated substrate resulting from the pretreatment step f), or by a solid/liquid separation, optionally coupled with a washing, carried out after the enzymatic hydrolysis step g).

Step i) of Separating the Solvents and/or Alcohols from the Fermentation Must

The process according to the invention can finally comprise a step i) of separating the product(s) of interest from the fermentation must, optionally preceded by a solid/liquid separation step in order to remove at least one fraction of the solid matter contained in the fermentation must.

Preferably the step of separating the product(s) of interest, for example ethanol, uses one or more distillations, according to technology well known to those skilled in the art.

Other features and advantages of the invention will become apparent on reading the description of particular exemplary embodiments of the invention, given solely by way of illustration, and with reference to the abovementioned FIGS. 1 to 7.

Figure 1:
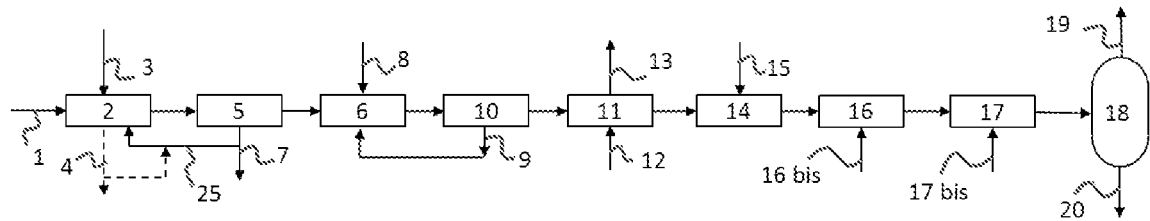
FIG. 1 represents a block diagram representing an embodiment of the process for producing solvents and/or alcohols from lignocellulosic biomass incorporating a step b) of washing the ground biomass according to the invention.

In FIG. 1, the ground lignocellulosic biomass particles enter through line 1 into the washing zone 2 to carry out the washing step b). The washing according to the invention is carried out by means of washing water (water with a pH between 4 and 8.5) supplied via line 3. A first filtrate which corresponds to a free used washing water can optionally be separated, for example by draining and recovered via line 4.

The washed lignocellulosic biomass is then subjected to the solid/liquid separation step c) (separation zone 5), which preferably carries out a pressing of the wet pulp. Preferably, this solid/liquid separation is carried out concomitantly with the transfer of the washed lignocellulosic biomass to the impregnation zone 6 in order to carry out step d) of the process. The solid/liquid separation produces a used washing water which is extracted through line 7 and a washed lignocellulosic substrate, the dry matter content of which is between 15% and 70% by weight. In the embodiment of FIG. 1, the used washing waters from lines 4 and 7 are optionally mixed in order to be recycled to the washing step via line 25. Preferably, only a portion of the used washing water resulting from the separation c) is optionally recycled to washing step b), and all or some of the used washing water is used in steps downstream of the pretreatment which are described with the aid of the following figures.

The washed lignocellulosic substrate is then sent to the impregnation zone 6 in which the step d) of impregnation with an acid liquor, which is supplied via line 8, is carried out. The impregnation is carried out in an impregnation reactor at a temperature between 10° C. and 90° C., and preferably at atmospheric pressure. The residence time of the lignocellulosic substrate in the impregnation reactor is usually from 10 seconds to 180 minutes, preferably between 30 seconds and 60 minutes, and more preferentially still between 30 seconds and 15 minutes. Preferably, the impregnation step is carried out in a single step with a dry matter content of between 1% and 30%.

The washed and impregnated lignocellulosic substrate, withdrawn from the impregnation zone 6, is transferred to a solid/liquid separation zone 10 in order to separate a used acid liquor via line 9 and a washed and acidified lignocellulosic substrate which is sent to the pretreatment step. The solid/liquid separation preferably carries out a pressing which is performed concomitantly with the transport of the washed and impregnated lignocellulosic substrate to the pretreatment unit 11, for example by means of a screw of the "plug screw feeder" type. The used acid liquor (or pressate resulting from the pressing) is recovered in line 9 and is optionally recycled to the impregnation zone 6. Impregnation with the acid liquor makes it possible to obtain a product having a dry matter content generally of between 15% and 70% by weight and the pH of which is between 0.1 and 3.

The pretreatment unit 11 shown in FIG. 1 carries out a steam explosion process. Thus the steam is supplied through line 12 while the expanded steam is drawn off through line 13 and is generally condensed in order to provide an acid condensate.

Preferably and as shown in FIG. 1, the pretreated lignocellulosic substrate is neutralized in the neutralization zone 14 which is supplied through line 15 with a neutralizing solution such as a basic solution.

The neutralized substrate is then subjected to enzymatic hydrolysis carried out in zone 16 in the presence of an enzyme cocktail supplied by line 16a suitable for hydrolyzing in particular cellulose into fermentable sugars (essentially glucose).

The product of enzymatic hydrolysis, referred to as hydrolyzate, is treated in a fermentation step in the fermentation zone 17 in order to convert, in the presence of fermentation microorganisms supplied by line 17a, the sugars into products of interest such as a solvent and/or an alcohol. The fermentation step carried out in the presence of microorganisms can be an ethanol fermentation mainly producing ethanol, a fermentation of the ABE or IBE type.

It should be noted that the enzymatic hydrolysis and fermentation steps can be carried out concomitantly according to a process denoted by the term "Simultaneous Saccharification and Fermentation (SSF)" known to those skilled in the art.

The fermentation must which is recovered at the outlet of the fermenter is treated with a view to separating the products of interest. Generally, the recovery of the fermentation products is carried out by distillation by means of a column 18, in a manner known to those skilled in the art. From column 18, a stream 19 that has concentrated the products of interest and a vinasse 20 are withdrawn.

Figure 2:
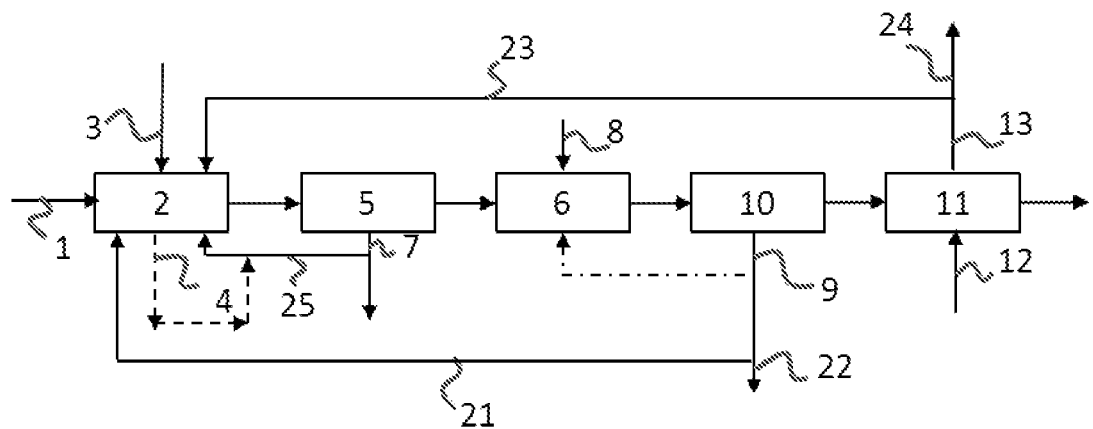
FIG. 2 is a block diagram representing an embodiment of the process for treating lignocellulosic biomass incorporating a recycling of various acid effluents.

FIG. 2 represents a diagram of the process for treating lignocellulosic biomass, represented in which are streams which can be recycled to the biomass washing step b) and separation step c), in addition to the external stream of washing water which is conveyed by line 3.

As indicated in FIG. 2, a portion 21 of the used acid liquor 9 resulting from the solid/liquid separation carried out in zone 10 before the pretreatment 11 can be recycled, the other portion 22 being purged or sent back to the impregnation step carried out in zone 6.

The washing step can also use a portion 23 of the acid condensates 13 resulting from the pretreatment 11 while the other portion 24 of the condensates is purged. When such recycling of the condensate is envisaged, it is possible to purify it, in particular in order to limit the contents of furfural compounds and of acetic acid before recycling it to the washing step.

As indicated previously, it is possible to recycle via line 25 at least one portion of the used washing water 7 which results from the separation step of zone 5.

The various recycling methods described can of course be combined with one another. When provision is made to recycle acid effluents to form part of the aqueous washing solution from step b), their contribution is adjusted so that the aqueous solution remains at the desired pH (of at least 4, and in particular of at least 6).

Figure 3:
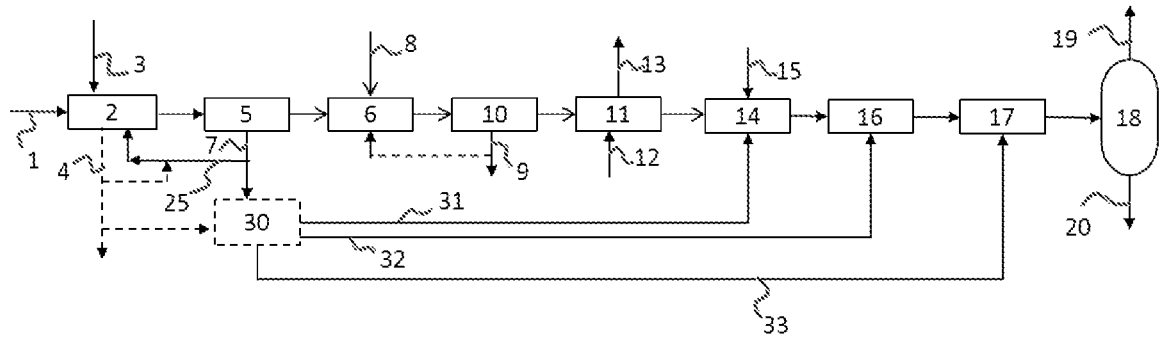
FIG. 3 is a block diagram representing an embodiment of the process for producing alcohols and/or solvents from lignocellulosic biomass incorporating a recycling of the water used for the washing of the ground biomass, to the downstream neutralization and/or enzymatic hydrolysis and/or fermentation steps according to the invention.

FIGS. 3 and 4, which are similar to FIG. 1, show a diagram of the process for producing solvents and/or alcohols from lignocellulosic biomass comprising a biomass washing step b) in which the used washing water is not only recycled to the washing step, but advantageously also, completely or partially, used in downstream steps.

Indeed, this used washing water that is very rich in minerals (ash) can be advantageously used as a source of nutrients for the microorganisms and yeasts.

The pH of the washing water is between 4 and 8.5. Thus, depending on the pH, it is advisable to carry out a neutralization, if necessary, if this water is intended for the production of enzymes or yeasts or for supplementing the enzymatic hydrolysis or fermentation media.

FIG. 3 also shows the various possible uses of the used washing water drawn off through lines 4 and/or 7. All or a portion of the used washing water 7 (and/or 4) can be sent to an optional treatment step 30, for example a pH adjustment and/or detoxification treatment step. The used washing water or the effluent from the treatment step 30 can be sent to the pretreated lignocellulosic substrate neutralization step 14 via line 31, to the enzymatic hydrolysis step of zone 16 via line 32 and/or to the fermentation step 17 via line 33.

FIG. 4 illustrates the options for using the used washing water resulting from the separation step c) in the steps for producing enzymes and/or yeasts when these steps are integrated into the biomass treatment process. FIG. 4 also shows a possible recycling of the used washing water to an optional washing step (partial or complete) of the pretreated lignocellulosic substrate, it being possible for this washing step to be preceded or followed by the step of neutralizing the pretreated lignocellulosic substrate.

It should be noted that the process from FIG. 4 combines the two types of recycling (production of enzymes and/or yeasts and optional washing step). However, in the context of the invention, it is quite possible to carry out only one of the two types of recycling.

With reference to FIG. 4, the pretreated lignocellulosic substrate is sent to the washing step (additional step with respect to FIG. 3) carried out in zone 40, before the neutralization step of zone 14. The washing water is supplied by line 41. A liquor containing soluble sugars and other components is recovered via line 42.

This sugar-rich liquor can be used for the production of enzymes carried out in zone 44 and/or of yeasts carried out in zone 45. The enzymes and the yeasts produced are added respectively via lines 46 and 47 to the enzymatic hydrolysis step in zone 16 and to the fermentation step in zone 17.

The used washing water 7 (this is also the case, optionally, for the washing water 4) can be treated in an optional treatment step 30 (detoxification and/or neutralization) and be sent in whole or in part via lines 43 and 48 to the pretreated lignocellulosic substrate washing step 40, in addition to or as a replacement for the washing water of line 41. The used washing water 7 (and optionally also the washing water 4) can also be sent to the enzyme production unit 44 via line 49 and/or to the yeast production unit 45 via line 50. The washing waters 4 and 7 can be mixed before or after the optional treatment step 30. The portion of the used washing water 7 which is optionally not recycled can be purged through line 26.

The washing water 7 (and 4) resulting from the washing and the separation b)+c) of the invention can therefore be reintroduced at several stages of the process after the pretreatment and/or during the manufacture of the enzymes and/or yeasts, and optionally also partially recycled for the washing step b). This choice depends on the type of plant (integrated or non-integrated production of enzymes and yeasts), on the type of biomass, etc., and can therefore fluctuate from one production cycle to another or within the same cycle.

According to one embodiment, the steps of neutralization and enzymatic hydrolysis are carried out in the same unit.

In summary, the implementation of the lignocellulosic biomass washing step has the advantage of reducing the amount of acid required for the impregnation. This reduction consequently makes it possible to limit the additions of basic compounds for the step of neutralizing the pretreated lignocellulosic substrate, which at the same time reduces the amount of salts formed. However, these salts (in particular sulfates) considerably limit the recycling of the streams, especially in the presence of microorganisms.

The fact of generating a washing water whose pH is buffered, and which is subsequently recycled, allows savings to be made in terms of operating expenses, while avoiding pH shocks that are harmful to the functioning of the microorganisms and enzymes, and also for the survival of the yeasts. The reuse of used washing water is very flexible to implement according to the various plant configurations, and provides a real advantage to very specific steps of the process downstream of the pretreatment.

EXAMPLES

Example 1: Assaying of the Residual Acidities in Liquors Prepared According to the Prior Art and According to the Invention Preparation of the Fresh Liquor:

600.2 g of acid solution were prepared by mixing 4.6 g of $H_2SO_4$ solution concentrated to 72% by weight of $H_2SO_4$ with water. The acid liquor thus obtained is referred to as "Liquor L1".

Obtaining a Used Impregnation Liquor (Comparative):

247.3 g of the above liquor were heated to 60° C. and then brought into contact for a period of approximately 180 minutes with 30 g of ground straw, the dry matter (DM) content of which was 92.4%. This impregnation was therefore carried out at a dry matter (DM) content of 10% by weight with a supply of $H_2SO_4$ of 4.9 g $H_2SO_4$/100 g DM. At the end of the contacting, a weight loss of 20.6 g during the impregnation is noted. The acid-impregnated biomass is then pressed, generating 90 g of a wet cake and 156.5 g of a used impregnation liquor referred to as "Liquor L2".

Used Impregnation Liquors (According to the Invention):

The same ground straw (30 g) is brought into contact with water at 60° C. for 3 minutes simulating washing of the biomass. The dry matter (DM) content is 10% by weight in this mixture. The medium is then separated by pressing so as to recover a washed straw and a used washing water (filtrate). Experimental losses are noted: less than 0.02% losses during contact with water and around 5% weight losses during separation, linked to the experimental setup (2.2% on a DM basis).

Table 1 below gives the experimental data for preparing the straw washed with water: 50.1

| | |
|---|---|
| Dry matter content of raw straw (wt %) | 92.4 |
| Weight of washed raw straw (g) | 30.0 |
| Weight of water at 60° C. (g) | 250.5 |
| Dry matter content of the mixture before washing (wt %) | 9.9 |
| pH of the water at lab T° C. | 7.40 at 23° C. |
| pH of the water at 60° C. | 7.63 at 58° C. |
| Washing time | 3 min |
| Total weight before washing (g) | 280.5 |
| Total weight before pressing (g) | 280.2 |
| Weight of solid after pressing (g) | 74.8 |
| Dry matter content of the pressed solid (wt %) | 34.3 |
| Weight of the water after pressing (g) | 191.2 |
| Dry matter content of the water after pressing (wt %) | 0.77 |
| pH of the water after pressing (—) | 6.96 at 34° C. | g of straw washed as described above, having a DM content of 34.3%, are brought into contact for 180 minutes with 121.7 g of an acid liquor containing 0.70% by weight of $H_2SO_4$. This impregnation was therefore carried out at 10% by weight of dry matter (DM), and with a supply of $H_2SO_4$ of 4.96 g $H_2SO_4$/100 g DM. At the end of the contacting, a weight loss of 24.8 g during the impregnation is noted. The washed and acid-impregnated biomass is then pressed so as to obtain 57.9 g of a wet cake and 73.1 g of a used acid impregnation liquor which is referred to as "Liquor L3".

The acidity of these 3 liquors was assayed by monitoring the change in pH as a function of the volume of basic solution added. The basic solution used is a 0.1N NaOH solution. FIG. 5 shows the titration curves obtained for each liquor, with, on the x-axis, the amount of 0.1N NaOH solution in ml per ml of sample, and, on the y-axis, the pH.

It is noted that the impregnation step leads to a loss of acidity of the liquor L1. During the impregnation, after the washing according to the invention, it is seen that the used liquor L3 recovered has a higher acidity than the used liquor L2 for a similar specific amount of acid catalyst introduced. Thus, the "consumption" of acidity by the biomass is reduced, thanks to the implementation of the washing prior to the impregnation according to the present invention.

Example 2: Readjustment of the pH with a View to Recycling the Liquors Prepared According to the Prior Art and According to the Invention The ground straw from example 1 is brought into contact with water at 60° C. for 60 min. The DM content is 10% by weight in this mixture. The medium is then separated by a solid/liquid separation making it possible to recover a washed straw and a washing water (filtrate). The experimental losses were close to 12% weight losses during soaking (most likely by evaporation) and approximately 3% weight losses during separation, linked to the experimental setup. The DM balance of the preparation is itself 96.6%.

Table 2 below gives the experimental data for preparing the straw washed with water:

| | |
|---|---|
| Dry matter content of raw straw (wt %) | 92.4 |
| Weight of washed raw straw (g) | 30.0 |
| Weight of water at 60° C. (g) | 251.0 |
| DM content of the mixture before washing (wt %) | 9.9 |
| pH of the water at lab T° C. | 7.38 at 23° C. |
| pH of the water at 60° C. | 7.35 at 57° C. |
| Washing time | 60 min |
| Weight of solid after pressing (g) | 85.2 |
| DM content of the pressed solid (wt %) | 29.4 |
| Weight of the water after pressing (g) | 156.6 |
| DM content of the water after pressing (wt %) | 1.1 |
| pH of the water after pressing (—) | 7.16 at 20° C. |

50.1 g of straw washed as described above, the DM content of which is 29.4%, are brought into contact for 180 minutes with 97.1 g of an acid liquor containing 0.75% by weight of $H_2SO_4$. This impregnation was therefore carried out at 10% by weight of DM and with an amount of $H_2SO_4$ of 4.93 g $H_2SO_4$/100 g DM. This mixture is then pressed, making it possible to obtain 67.2 g of a wet cake and 48.6 g of a used acid impregnation liquor "liquor L4".

The pH of the used liquors L2 and L4 was readjusted to a target value of 1.2 by adding a 0.05M $H_2SO_4$ solution. The change in pH as a function of the volume added is presented in FIG. 6, with, on the x-axis, the number of ml of 0.05M $H_2SO_4$ solution per ml of sample.

The used liquor prepared according to the invention (Liquor L4) requires a smaller amount of acid than the used liquor obtained after impregnation of the unwashed biomass (Liquor L2) in order to lower its pH with a view in particular to the recycling thereof.

Thus, to adjust the pH of the used liquors to a pH of 1.2, it is necessary to add 3.8 mg of sulfuric acid/ml of sample for the used liquor L4 and 5.3 g/ml of sample for the used liquor L2, i.e. an increase of 28% in the consumption of sulfuric acid.

Example 3: Biomass Analyses Before and After the Sequence of the Impregnation and Pretreatment Steps (Prior Art)

A wheat straw harvested in 2017 was ground and then analyzed after grinding. The contents of the minerals copper, zinc, magnesium and manganese of this batch of straw A are reported in table 3 below, expressed in mg of the element/dry kg of straw:

| Sample analyzed | | Native straw A |
|---|---|---|
| Dry matter content | wt %/raw | 92% |
| Copper | mg Cu/dry kg | 2 |
| Zinc | mg Zn/dry kg | 4 |
| Magnesium | mg Mg/dry kg | 778 |
| Manganese | mg Mn/dry kg | 34 |

This ground straw was then pretreated according to a process of the prior art: steam explosion preceded by acid impregnation, with total recycling of the used impregnation liquor. Thus, the ground straw is conveyed into an impregnation tool by means of a plug-screw type screw. The straw throughput is 2820 kg/hour, i.e. 2600 dry kg/hour. It is expanded in a bed of acid liquor and conveyed vertically into the impregnation tool, from which it emerges saturated with impregnation liquor. A tank of acid liquor is used for the preparation of the liquor which continuously feeds the impregnation tool in order to renew the stock and keep the level constant. This impregnated straw is then conveyed to a steam explosion tool. It is introduced into this tool by means of a plug-screw type screw. During the compression of the impregnated straw in the screw, used liquor is expelled (referred to as pressate). This liquor is completely recycled to the acid liquor preparation tank. This acid liquor preparation tank is also supplied with water and sulfuric acid $H_2SO_4$ in order to compensate for the loss of the liquor fraction which is exported with the straw to the steam explosion tool.

After a short cooking time in the reactor, the impregnated and cooked straw is expanded at the reactor outlet. The mixture consisting of solid, liquid and vapor is separated in a cyclone, allowing the vapor to be separated from the solid/liquid mixture. This solid/liquid mixture constitutes the pretreated straw. The conditions applied for the impregnation and steam explosion are:

Flow rate of concentrated acid solution: 116 kg/h on average
Water flow rate: 3900 kg/h
Impregnation time: 1 min 30
Cooking residence time: 5 min
Steam supply: 100% at the top
Pressate recycling: 100%

The average flow rate of acid solution is reported above, the fluctuations are around 15% to 20% about this average flow rate (minimum 88 kg/h, maximum 130 kg/h).

A sample of pretreated straw was analyzed. The contents of the minerals copper, zinc, magnesium and manganese of the pretreated straw are reported in table 4 below, expressed in mg of the element/dry kg of pretreated straw.

Compared to the native straw, the copper, zinc and magnesium contents are considered to be stable, and the manganese content has been reduced by 30%.

| Sample analyzed | | Pretreated straw A |
|---|---|---|
| Dry matter content | wt %/raw | 38% |
| Copper | mg Cu/dry kg | 3 |
| Zinc | mg Zn/dry kg | 6 |
| Magnesium | mg Mg/dry kg | 706 |
| Manganese | mg Mn/dry kg | 24 |

Example 4: Analysis of Biomasses Before and After the Sequence of the Washing, Impregnation and Pretreatment Steps (in Accordance with the Invention)

A wheat straw harvested in 2013 was ground and then analyzed after grinding. The contents of the minerals copper, zinc, magnesium and manganese of this batch of straw B are reported in table 5 below, expressed in mg of the element/dry kg of straw:

| Sample analyzed | | Native straw B |
|---|---|---|
| Dry matter content | wt %/raw | 89% |
| Copper | mg Cu/dry kg | 2 |
| Zinc | mg Zn/dry kg | 4 |
| Magnesium | mg Mg/dry kg | 760 |
| Manganese | mg Mn/dry kg | 35 |

This ground straw was then pretreated according to a process according to the invention: washing of the biomass with an aqueous solution, then acid impregnation followed by a steam explosion, with total recycling of the used impregnation liquor.

Thus, the ground straw is conveyed to a first washing step. The straw throughput is 2920 kg/hour, i.e. 2600 dry kg/hour. In this step, the ground straw is brought into contact with an aqueous solution of pH 5 for a period of 8 minutes in a rotary tool allowing the simultaneous washing and draining of the straw. Here, the washing step b) and liquid/solid separation step c) are carried out in the same tool. A first washing stream is extracted from the rotary tool and the drained straw is conveyed to the following impregnation step. It is introduced into the impregnation tool by means of a plug-screw type screw. Due to the high moisture content of the drained straw, the compression in this screw generates a second washing stream: there is therefore here a separation according to step c) in two operations. After this solid/liquid separation, the straw has a dry matter content of 55%. It is expanded in a bed of acid liquor and conveyed vertically into the impregnation tool, from which it emerges saturated with impregnation liquor. A tank of acid liquor is used for the preparation of the liquor which continuously feeds the impregnation tool in order to renew the stock and keep the level constant. This impregnated straw is then conveyed to a steam explosion tool. It is introduced into this tool by means of a plug-screw type screw. During the compression of the impregnated straw in the screw, used liquor is expelled (referred to as pressate). 95% of the mass flow of this liquor is recycled to the acid liquor preparation tank, and the remaining 5% supplies the aqueous washing solution preparation tank. The acid liquor preparation tank is also supplied with water and sulfuric acid $H_2SO_4$ in order to compensate for the loss of the liquor fraction which is exported with the straw to the steam explosion tool. The aqueous washing solution preparation tank is supplied with used liquor and water.

After a short cooking time in the reactor, the impregnated and cooked straw is expanded at the reactor outlet. The mixture consisting of solid, liquid and vapor is separated in a cyclone, allowing the vapor to be separated from the solid/liquid mixture. This solid/liquid mixture constitutes the pretreated straw.

The conditions applied for the washing are chosen to approximate the conditions of dilute static impregnation (i.e. 8% DM in the straw):

Flow rate of aqueous washing solution: 29 500 kg/h on average
Water flow rate: 29 100 kg/h
Contact time: 8 min
The conditions applied for the impregnation and steam explosion are:
Flow rate of concentrated acid solution: 65 kg/h on average
Water flow rate: 1590 kg/h
Impregnation time: 1 min 30
Cooking residence time: 5 min
Steam supply: 100% at the top
Pressate recycling: 95% to acid liquor preparation and 5% to aqueous solution The average flow rate of acid solution is reported, the fluctuations are 10% about this average flow rate (minimum 58 kg/h, maximum 72 kg/h).

A sample of pretreated straw was analyzed. The contents of the minerals copper, zinc, magnesium and manganese of the straw washed then pretreated according to the invention are reported in table 6 below, expressed in mg of the element/dry kg of pretreated straw:

| Sample analyzed | | Straw B washed then pretreated |
|---|---|---|
| Dry matter content | wt %/raw | 38% |
| Copper | mg Cu/dry kg | 1 |
| Zinc | mg Zn/dry kg | <1.5 |
| Magnesium | mg Mg/dry kg | 43 |
| Manganese | mg Mn/dry kg | 19 |

Compared to native straw, the copper, zinc, magnesium and manganese contents have been greatly reduced due to the leakage of these minerals into the used washing water. In particular, more than 90% of the magnesium initially present in the native straw is no longer present in the straw washed and pretreated according to a process in accordance with the invention.

The implementation of washing prior to the impregnation in accordance with the invention therefore allows a reduction in the acid consumption of 44% relative to the average flow consumed and an improvement in the stability of this consumption. This example therefore demonstrates both the improvement in acid consumption and the leakage of minerals into the used washing waters.

Example 5: Demonstration of the Beneficial Effect of Minerals on the Growth of Yeast-Type Microorganisms A sample of washed and pretreated straw produced according to example 4 was used for laboratory work. First of all, this sample underwent a solid/liquid extraction in order to extract therefrom a sugary liquor containing 65 g/kg of glucose and xylose sugars.

This liquor was then used as a substrate for a laboratory yeast propagation test. The tests take place in a baffled flask with a total volume of 250 ml, fitted with cellulose stoppers allowing air to pass through and placed on a shaker table. The temperature and pH are regulated at the same setpoint for all the tests. The extracted liquor is supplemented:
For test 1, with 2.5 g/kg of diammonium phosphate and 2 g/kg of urea
For test 2, with 2.5 g/kg of diammonium phosphate, 2 g/kg of urea and 2 g/kg of the mineral cocktail. The composition of the mineral cocktail is given in table 7 below:

| Compound | Concentration g/kg |
|---|---|
| $MgSO_4 \cdot 7H_2O$ | 370 |
| $CuSO_4 \cdot 2H_2O$ | 0.15 |
| $MnCl_2 \cdot 4H_2O$ | 0.30 |
| $ZnSO_4 \cdot 7H_2O$ | 1.0 |

After supplementing and setting the pH, the liquors are inoculated with a yeast of Saccharomyces cerevisiae type genetically modified to assimilate xylose (C5 sugar), in addition to the natural assimilation of glucose. The inoculation is carried out at the same content in the tests, and the monitoring of cell growth is carried out by measuring the absorbance (OD at 600 nm) during the test, and by measuring the insolubles in a sample for the final time of the test. FIG. 7 shows the monitoring of the absorbance A as a function of the time expressed in hours, for test 1, which is represented by squares, and for test 2, which is represented by triangles.

The final yeast contents are 13.3 g/kg for test 1 versus 17 g/kg for test 2. A beneficial impact of minerals on the growth of this Saccharomyces type yeast is thus demonstrated.

The invention claimed is:
1. A process for treating lignocellulosic biomass comprising the following successive steps:
a) conditioning the lignocellulosic biomass by at least one grinding step to obtain particles of ground biomass;
b) washing said particles with an aqueous solution having a pH of between 4 and 8.5, at a temperature of between 10° C. and 95° C., at atmospheric pressure, and for a period of between 1 and 300 minutes;
c) separating the aqueous solution from the washed biomass particles in order to obtain a lignocellulosic substrate having a dry matter content of between 15% and 70% by weight, and a used aqueous washing solution;
d) impregnating said lignocellulosic substrate with an acidic liquor, so as to obtain an impregnated lignocellulosic substrate having a pH of between 0.1 and 3;
e) carrying out a solid/liquid separation of the impregnated lignocellulosic substrate, in order to obtain a lignocellulosic substrate having a dry matter content of between 15% by weight and 70% by weight, and a liquid effluent;
f) pretreating said impregnated lignocellulosic substrate resulting from step e) by cooking, so as to obtain a pretreated lignocellulosic substrate;
g) carrying out an enzymatic hydrolysis of the pretreated lignocellulosic substrate with enzymes produced from fungus microorganisms, so as to obtain a hydrolyzate containing sugars;
h) carrying out a fermentation, by bacteria or yeast microorganisms, of the hydrolyzate resulting from step g) in order to obtain a fermentation must containing at least one biobased molecule;
a step of neutralizing the lignocellulosic substrate pretreated in step f), before or during the enzymatic hydrolysis step g), and at least one portion of the used aqueous washing solution separated in step c) is introduced into said neutralization step;
and introducing at least one portion of the used aqueous washing solution separated in step c) into a step of said biomass treatment process which is after the pretreatment step f), or into an enzyme production step or into a step of producing/propagating the microorganisms for steps g) or h) when at least one of these enzyme production or microorganism production/propagation steps is integrated into said biomass treatment process or a combination thereof.

2. The process as claimed in claim 1, wherein at least one portion of the used aqueous washing solution separated in step c) is introduced into the enzymatic hydrolysis step g) or into the fermentation step h).

3. The process as claimed in claim 1, further comprising an integrated step of producing, by fungus microorganisms, the enzymes for the enzymatic hydrolysis of step g), and at least one portion of the used aqueous washing solution separated in step c) is introduced into said enzyme production step.

4. The process as claimed in claim 1, further comprising an integrated step of propagating bacteria or yeast microorganisms for the fermentation of step h), and at least one portion of the used aqueous washing solution separated in step c) is introduced into said propagation step.

5. The process as claimed in claim 1, wherein the duration of the washing step b) is between 1 and 60 minutes.

6. The process as claimed in claim 1, wherein the aqueous solution of the washing step b) has a pH of between 5.5 and 7.5.

7. The process as claimed in claim 1, wherein the aqueous solution of the washing step b) is at a temperature of between 25° C. and 90° C.

8. The process as claimed in claim 1, wherein the amount of aqueous solution supplied to the washing step b) is between 0.5 and 60 g/g biomass.

9. The process as claimed in claim 1, wherein a portion of the used aqueous washing solution separated in step c) is reintroduced into the washing step b).

10. The process as claimed in claim 1, wherein a portion of the liquid effluent resulting from step e) is introduced into the washing step b).

11. The process as claimed in claim 1, wherein, in step f), a steam explosion pretreatment is carried out in order to obtain a vapor and the pretreated lignocellulosic substrate.

12. The process as claimed in claim 11, wherein vapor resulting from step f) is condensed so as to produce an acid condensate, and at least one portion of the acid condensate, alone or as a mixture with water, is introduced into the washing step b).

13. The process as claimed in claim 1, wherein, integrated into said process is a step of producing enzymes or a step of producing/propagating the microorganisms for steps g) or h) or a combination thereof, and a step is provided for extracting at least one portion of the sugary liquors obtained after the pretreatment step f) or after the enzymatic hydrolysis step g).

14. The process as claimed in claim 13, wherein at least one portion of the used aqueous washing solution resulting from step c) is introduced for the extraction of the sugary liquors by washing.

15. The process as claimed in claim 1, wherein, in step a), the conditioning of the lignocellulosic biomass by at least one grinding step achieves obtaining particles of ground biomass having a size of at most 300 mm.

16. The process as claimed in claim 1, wherein, step f) of pretreating said impregnated lignocellulosic substrate resulting from step e) by cooking, is performed for a period of 1 to 120 minutes.

17. The process as claimed in claim 1, wherein, in step h), the at least one biobased molecule is a solvent or an alcohol or a combination thereof.

18. The process as claimed in claim 1, wherein, in step f), a steam explosion pretreatment is carried out in order to obtain a vapor and the pretreated lignocellulosic substrate for a period of at most 30 minutes.

19. The process as claimed in claim 1, wherein, integrated into said process is a step of producing enzymes or a step of producing/propagating the microorganisms for steps g) or h) or a combination thereof, and a step is provided for extracting at least one portion of the sugary liquors obtained after the pretreatment step f) or after the enzymatic hydrolysis step g) by washing the substrate with an aqueous solution.

20. The process as claimed in claim 1, further comprising integrating into said process a step of producing enzymes or a step of producing/propagating the microorganisms for steps g) or h) or a combination of g) and h), or a combination of the integrating into said process a step of producing enzymes and the step of producing/propagating the microorganisms.

* * * * *